United States Patent
Okamoto et al.

(10) Patent No.: US 9,585,398 B2
(45) Date of Patent: *Mar. 7, 2017

(54) DISINFECTANT

(71) Applicant: MARUISHI PHARMACEUTICAL CO., LTD., Osaka (JP)

(72) Inventors: Kazuki Okamoto, Osaka (JP); Junji Okunishi, Osaka (JP); Yutaka Nishihara, Osaka (JP); Masahiko Seto, Osaka (JP)

(73) Assignee: MARUISHI PHARMACEUTICAL CO., LTD, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/616,455

(22) Filed: Feb. 6, 2015

(65) Prior Publication Data

US 2015/0150265 A1 Jun. 4, 2015

Related U.S. Application Data

(63) Continuation of application No. 12/529,334, filed as application No. PCT/JP2008/053834 on Mar. 4, 2008, now Pat. No. 8,980,313.

(30) Foreign Application Priority Data

Mar. 9, 2007 (JP) ................................. 2007-059991

(51) Int. Cl.
| | |
|---|---|
| *A01N 59/16* | (2006.01) |
| *A01N 31/02* | (2006.01) |
| *A01N 37/36* | (2006.01) |
| *A61K 31/045* | (2006.01) |
| *A61K 31/191* | (2006.01) |
| *A61K 31/194* | (2006.01) |
| *A61K 31/315* | (2006.01) |

(52) U.S. Cl.
CPC ............ *A01N 59/16* (2013.01); *A01N 31/02* (2013.01); *A01N 37/36* (2013.01); *A61K 31/045* (2013.01); *A61K 31/191* (2013.01); *A61K 31/194* (2013.01); *A61K 31/315* (2013.01)

(58) Field of Classification Search
None
See application file for complete search history.

(56) References Cited

U.S. PATENT DOCUMENTS

| | | | | |
|---|---|---|---|---|
| 4,647,458 A | * | 3/1987 | Ueno ..................... | A01N 37/02 422/28 |
| 5,043,357 A | * | 8/1991 | Hoffler .................. | A01N 31/02 514/553 |
| 5,728,404 A | * | 3/1998 | von Rheinbaben .... | A01N 59/06 424/600 |
| 7,592,300 B2 | | 9/2009 | Taylor et al. | |
| 2005/0113276 A1 | | 5/2005 | Taylor et al. | |
| 2007/0184013 A1 | | 8/2007 | Snyder et al. | |
| 2007/0185216 A1 | * | 8/2007 | Snyder ................... | A01N 31/02 514/724 |
| 2008/0286223 A1 | | 11/2008 | Fuls et al. | |
| 2009/0012174 A1 | | 1/2009 | Seitz, Jr. et al. | |
| 2009/0018213 A1 | | 1/2009 | Snyder et al. | |
| 2009/0104281 A1 | | 4/2009 | Taylor et al. | |

FOREIGN PATENT DOCUMENTS

| | | |
|---|---|---|
| EP | 1266571 B1 | 12/2002 |
| JP | 63022171 A | 1/1988 |
| JP | 2005247779 A | 9/2005 |
| RU | 2220745 C2 | 1/2004 |
| WO | 2005051342 A1 | 6/2005 |
| WO | 2006062857 A2 | 6/2006 |
| WO | WO 2006062834 A2 * | 6/2006 |
| WO | WO 2006062845 A2 | 6/2006 |
| WO | 2007044032 A2 | 4/2007 |
| WO | 2007095008 A2 | 8/2007 |

OTHER PUBLICATIONS

Decision on Grant of Patent issued on Jul. 2, 2015 corresponding to Application No. 2011132893.

* cited by examiner

*Primary Examiner* — Abigail Fisher
*Assistant Examiner* — Daniel Branson
(74) *Attorney, Agent, or Firm* — Hogan Lovells US LLP

(57) ABSTRACT

A disinfectant comprising the following (a), (b), (c) and (d), but no other microbicidal disinfecting agents intended for microbicidal disinfection:
(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole disinfectant.

8 Claims, 2 Drawing Sheets

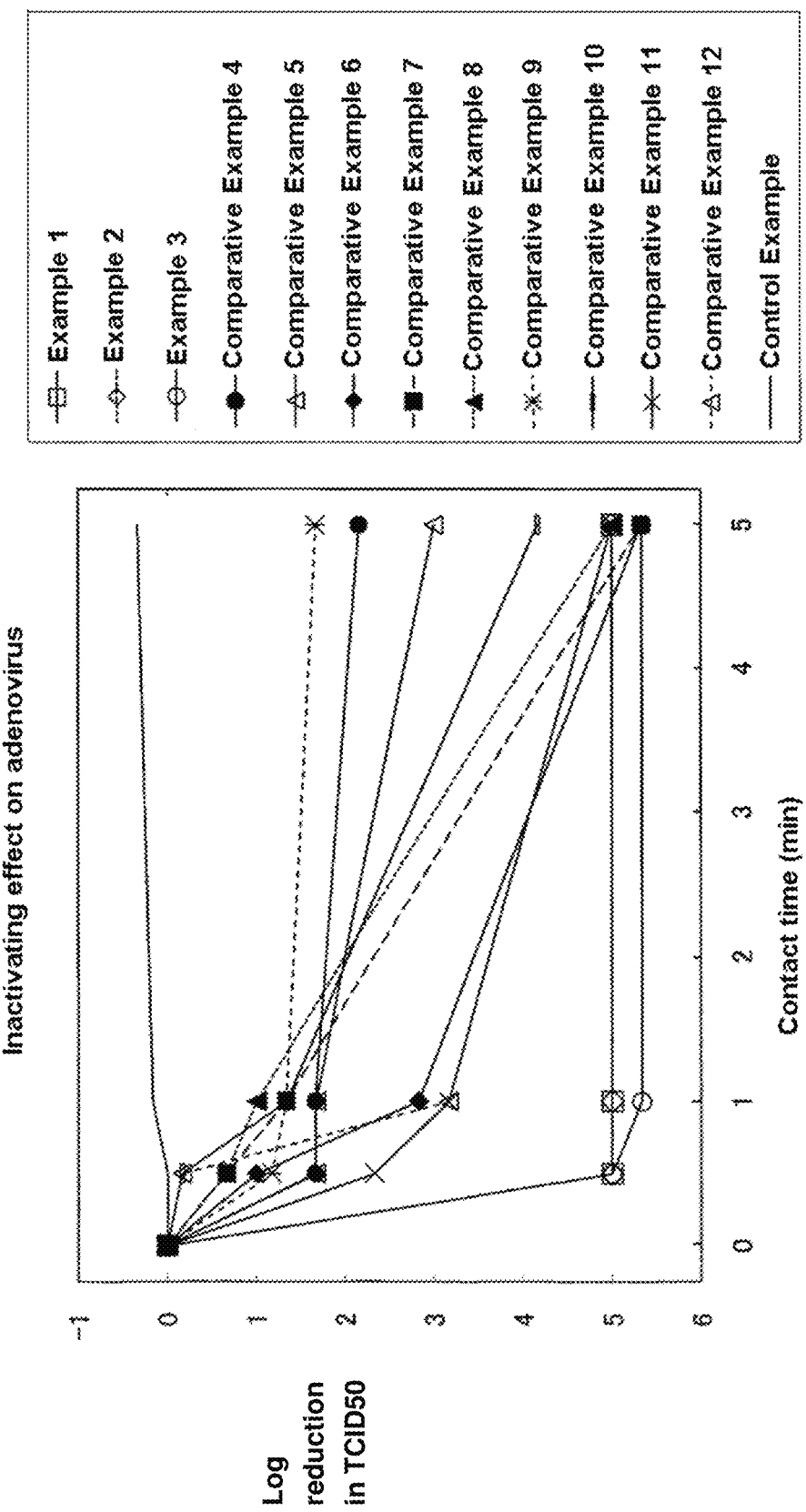

DISINFECTANT

RELATED APPLICATIONS

This application is a continuation application of U.S. Ser. No. 12/529,334, which was filed on Jan. 26, 2010, which was a national stage application of PCT/JP2008/053834, filed on Mar. 4, 2008, which claimed priority to Japanese Patent Application No. 2007-059991, filed on Mar. 9, 2007. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a disinfectant applicable to use for hands and skin, which has a virucidal activity as well as a fast-acting and persistent microbicidal activity.

BACKGROUND ART

It is known that addition of an organic acid to a lower alcohol such as ethanol enhances a microbicidal activity of ethanol preparations for food preservation.

For example, the patent literatures 1 and 2 individually disclose ethanol preparations for food preservation comprising ethanol, and an organic acid or a salt thereof, etc. The patent literatures 3 and 4 individually describe that microbicides comprising an alcohol such as ethanol and an organic acid can be used for hand wash and hand disinfection. The patent literature 5 discloses a sanitizing hand cleanser that can be used without water, comprising about 60 to 90% by weight of an organic alcohol, about 5 to 35% by weight of one or more silicone-based materials, about 5% by weight or less of one or more humectants, about 12% by weight or less of one or more additives for maintaining the skin pH, and one or more thickeners at such a concentration that the viscosity of the cleanser is within the range of 100 to 10,000 cp at about 25° C. The patent literature 6 discloses an alcohol preparation for reducing a population of microorganisms at low temperature, which is used for refrigerated or frozen foods, etc. and which comprises ethyl alcohol and phytic acid as essential ingredients.

Such ethanol preparations have a microbicidal activity, but the above literatures do not teach the activity of the preparations against viruses.

The patent literature 7 describes a method for disinfection, comprising contact with a 0.05 to 3% by weight aqueous solution of citric acid to inactivate a hepatitis virus B. In this method, lactic acid, malic acid and/or tartaric acid may be further added to the above solution. The patent literature 8 discloses a broad spectrum virucide comprising at least 70% by weight of ethanol and/or propanol, and 0.5 to 5% by weight of a short chain organic acid. The virucide in question has a short chain organic acid especially with 2 to 6 carbon atoms and is effective against a wide range of viruses, such as polioviruses, vaccinia viruses, SV40-viruses and adenoviruses. The literature also describes that this virucide can be used for hand disinfection as an example of its application.

The patent literature 9 discloses a virucidal disinfectant comprising an effective amount of a salt of metals belonging to alkali metals, alkaline earth metals, earth metals, and/or metals of the first, second or third secondary group of the periodic system of elements (transition element), in the form of an aqueous or alcoholic solution. In the Examples, the disinfectant was examined for its effectiveness against polioviruses, adenoviruses, vaccinia viruses and SV40 tumor viruses. The patent literature 10 discloses a method for reducing a population of a microorganism, comprising contact, at 5° C. or lower, with an aqueous alcoholic salt solution comprising 70 to 80 wt % alcohol; an alkali metal, an alkaline earth metal, zinc or a mixture thereof; a chloride or a phosphate; and the like, and the method reportedly showed a virucidal effect against adenoviruses etc., below the freezing point.

However, the virucides according to the patent literatures 7 to 10 are not satisfying enough to provide a fast-acting and persistent effect.

The patent literature 11 discloses a composition comprising (a) a divalent zinc salt as an essential ingredient, and optionally (b) an disinfecting alcohol, (c) an antimicrobial agent, and (d) an organic acid, wherein the composition has a pH of 5. This literature also discloses a method for reducing a bacteria and virus population, comprising contacting hands etc. with the composition for 30 seconds to achieve a log reduction of at least 4 against an acid-labile virus. The patent literature 12 discloses an anti-irritant composition comprising two or more water-soluble organic salts of zinc at concentrations of 0.1 to 2% (w/w), wherein the anti-irritant composition further comprises water, an alcohol and one or more agents selected from the group consisting of a gelling agent, a thickener, a hydrophilic or hydrophobic polymer, an emulsifier and an emollient. However, the composition according to the patent literature 11 or 12 also has room for improvement of its fast-acting and persistent effect.

The patent literature 13 discloses a pre-surgical disinfecting composition comprising a $C_{1-6}$ alcohol in an amount of at least about 50 mass % based on the total mass of the disinfecting composition; an acid selected from an inorganic acid, an organic acid and a mixture thereof; and a cationic oligomer or polymer, wherein the composition provides a log kill of greater than about 3 in less than about 3 minutes against resident and transient skin flora. The patent literature 13 also discloses that the composition may further comprise a transition metal compound such as a zinc compound as an auxiliary antimicrobial agent. However, this composition also has room for improvement of its fast-acting effect.

Patent Literature 1: JP-A 3-168075

Patent Literature 2: JP-A 63-22171

Patent Literature 3: JP-A 11-5734

Patent Literature 4: JP-A 2002-253188

Patent Literature 5: JP-A 2004-107667

Patent Literature 6: JP-A 7-298862

Patent Literature 7: JP-B 3761199

Patent Literature 8: JP-A 63-14702

Patent Literature 9: JP-W 7-504175

Patent Literature 10: U.S. Pat. No. 6,551,553

Patent Literature 11: WO2006/062845

Patent Literature 12: JP-W 2005-524634

Patent Literature 13: JP-A 2007-211012

SUMMARY OF INVENTION

Problem to be Solved by the Invention

An object of the present invention is to provide a disinfectant that has a virucidal activity and an excellent fast-acting and persistent antiseptic effect.

Means for Solving the Problem

The present inventors conducted extensive research to achieve the above-mentioned object. As a result, they found that
(i) a disinfectant comprising the following ingredients (a), (b), (c) and (d) is highly effective against non-enveloped viruses even without any further microbicidal disinfecting agent intended for microbicidal disinfection:
(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole disinfectant;
(ii) the disinfectant also has an excellent fast-acting and persistent effect; and
(iii) the disinfectant is also low irritant to skin when it comprises the above ingredients (a), (b), (c) and (d), but no other microbicidal disinfecting agents intended for microbicidal disinfection.

Namely, the present invention was completed based on the aforementioned findings, and provides the following disinfectants:
(1) a disinfectant comprising the following (a), (b), (c) and (d), but no other microbicidal disinfecting agents intended for microbicidal disinfection:
(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole disinfectant,
(2) the disinfectant according to the above (1), which is for virucidal use, and
(3) the disinfectant according to the above (1) or (2), which is for hand disinfection.

The present invention also provides the following methods and uses:
(4) a method for hand disinfection, which comprises contacting hands with a composition or applying a composition on hands, the composition comprising the following (a), (b), (c) and (d), but no other microbicidal disinfecting agents intended for microbicidal disinfection:
(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole composition,
(5) a method for killing a virus or inhibiting the growth thereof, which comprises contacting hands with a composition or applying a composition on hands, the composition comprising the following (a), (b), (c) and (d), but no other microbicidal disinfecting agents intended for microbicidal disinfection:
(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole composition,
(6) use of, as a disinfectant, a composition comprising the following (a), (b), (c) and (d), but no other microbicidal disinfecting agents intended for microbicidal disinfection:
(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole composition,
(7) use of, as a virucidal disinfectant, a composition comprising the following (a), (b), (c) and (d), but no other microbicidal disinfecting agents intended for microbicidal disinfection:
(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole composition,
(8) a composition for disinfection, comprising the following (a), (b), (c) and (d), but no other microbicidal disinfecting agents intended for microbicidal disinfection:
(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole composition, and
(9) a composition for killing a virus or inhibiting the growth thereof, comprising the following (a), (b), (c) and (d), but no other microbicidal disinfecting agents intended for microbicidal disinfection:
(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole composition.

Effect of the Invention

The disinfectant of the present invention comprises (a) ethanol and/or isopropanol, (b) lactic acid, (c) citric acid, and (d) a zinc-containing compound which releases zinc ion in solution, but no other microbicidal disinfecting agents intended for microbicidal disinfection. Such a disinfectant of the present invention is highly effective against non-enveloped viruses such as noroviruses, polioviruses and adenoviruses, against which disinfectant ethanol is ineffective. Further, the disinfectant of the present invention has an excellent virucidal activity, particularly against adenoviruses, because it comprises a zinc-containing compound which releases zinc ion in solution. Particularly, the virucidal activity against adenoviruses is not sufficiently provided by existing disinfectants, and this is a matter of concern in the clinical practice of the ophthalmology field.

In this view, the high virucidal effect brought by addition of a zinc-containing compound is of importance. Furthermore, the disinfectant of the present invention comprises no other microbicidal disinfecting agents intended for microbicidal disinfection than the above-mentioned ingredients, and therefore has an advantage of low irritancy to skin.

While the conventional disinfectants which comprise an alcohol and an organic acid are practically insufficient to exhibit a fast-acting and persistent effect, the disinfectant of the present invention has an extremely excellent fast-acting and persistent effect. Frequent use of disinfectants with high alcohol concentration easily causes skin roughness on hands, which results in less frequent hand-washing. However, due to the lack of persistent microbicidal effect, the conventional disinfectants which comprise an alcohol and an organic acid cannot provide sufficient disinfection on hands in less frequent hand-washing. In this respect, the disinfectant of the present invention, which has an excellent persistent effect, can sufficiently kill microorganisms on hands without frequent use. The skin roughness on hands is too serious a problem to ignore from a viewpoint of the measure against nosocomial infection since microbial flora easily occurs at sites with skin roughness. In this respect, the disinfectant of the present invention does not produce such a problem since it can be regularly used at longer intervals and thereby hardly causes skin roughness on hands. From these reasons, the disinfectant of the present invention can be used suitably for hand disinfection.

BRIEF DESCRIPTION OF DRAWINGS

FIG. 2 shows the comparison result of the median tissue culture infective dose (TCID50) among all the Examples and Comparative Examples, as a measure of the inactivating effect on adenovirus.

BEST MODE FOR CARRYING OUT THE INVENTION

Figure 1:
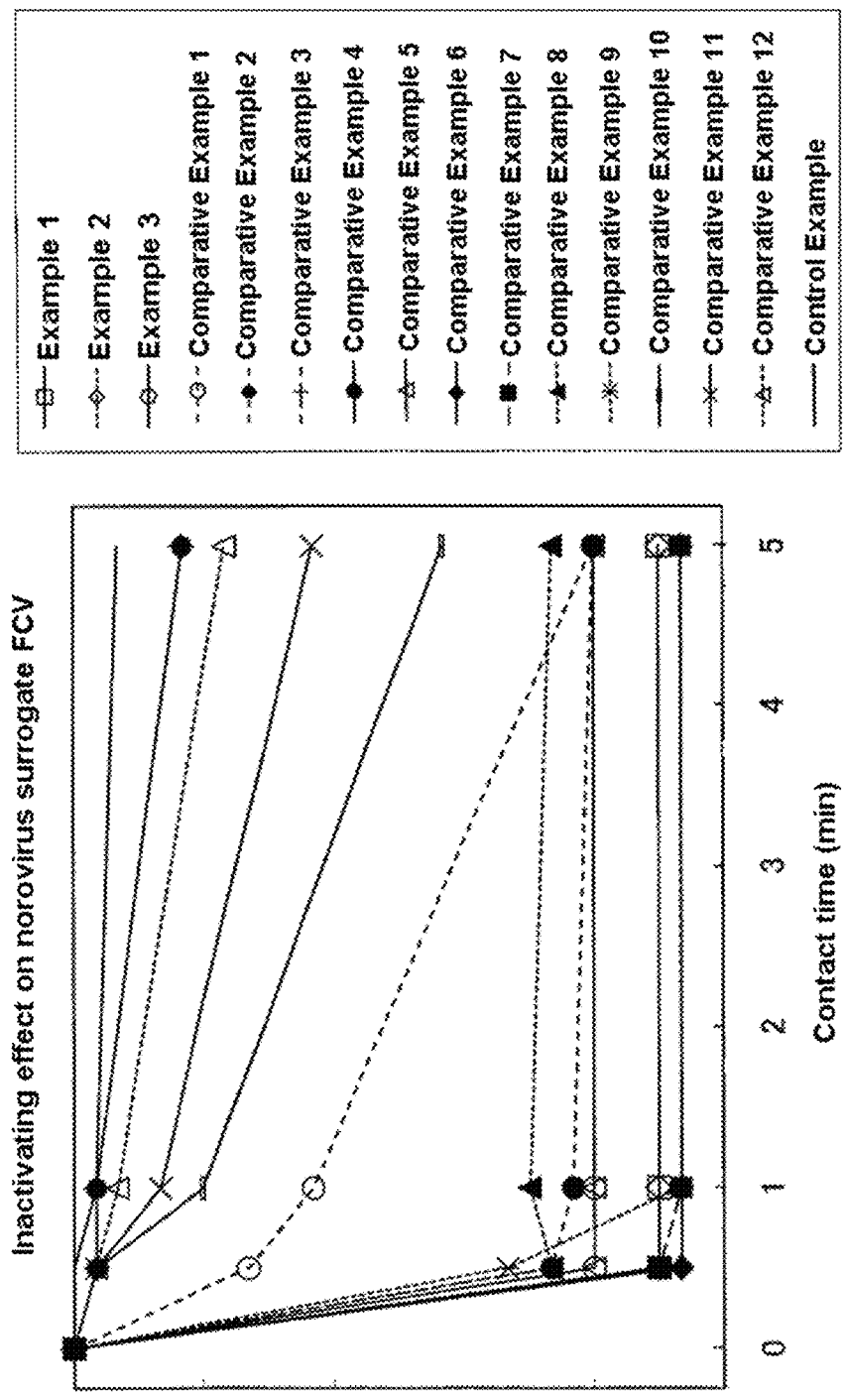
FIG. 1 shows the comparison result of the median tissue culture infective dose (TCID50) among all the Examples and Comparative Examples, as a measure of the inactivating effect on norovirus surrogate feline calicivirus.

Hereinafter, the present invention will be explained in detail. The disinfectant of the present invention comprises the following (a), (b), (c) and (d):
(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole disinfectant.

Alcohol

The alcohol of the present invention, a microbicidal ingredient of the disinfectant, is ethanol, isopropyl alcohol or a mixture of ethanol and isopropyl alcohol. Inter alia, ethanol alone or the combination of ethanol and isopropanol is preferred. Ethanol alone is particularly preferred.

The content ratio of ethanol, isopropyl alcohol or a mixture thereof is usually 40 to 90% (w/w), preferably about 50 to 90% (w/w), and more preferably about 50 to 85% (w/w) relative to the whole disinfectant. When the content ratio is within the above range, the disinfectant of the present invention is excellent in safety and solubility and is also effective. For example, when ethanol or isopropyl alcohol is used alone, the content ratio of ethanol or isopropyl alcohol is preferably 40 to 90% (w/w), and more preferably about 40 to 80% (w/w) relative to the whole disinfectant. When ethanol and isopropyl alcohol are used in combination, the content ratio of ethanol is preferably 40 to 90% (w/w), more preferably about 40 to 80% (w/w), and the content ratio of isopropyl alcohol is preferably 10% (w/w) or less, more preferably 5% (w/w) or less, relative to the whole disinfectant.

Organic Acid

The disinfectant of the present invention comprises specific organic acids, i.e., lactic acid and citric acid, which produce a synergistic effect with ethanol and/or isopropanol.

Therefore, the disinfectant has an enhanced fast-acting and persistent effect.

The content ratio of lactic acid is usually 0.1 to 2% (w/w), preferably about 0.1 to 1.5% (w/w), and more preferably about 0.1 to 1% (w/w) relative to the whole disinfectant.

The content ratio of citric acid is usually 0.01 to 2% (w/w), preferably about 0.01 to 1.5% (w/w), and more preferably about 0.01 to 1% (w/w) relative to the whole disinfectant.

When lactic acid and citric acid are present individually in the amounts ranging as above, their synergistic effect with ethanol and/or isopropanol is produced, and the disinfectant of the present invention has an enhanced fast-acting and persistent effect. The disinfectant also has a sufficient antiseptic effect as well as can be used safely for hands and skin.

Zinc-Containing Compound

The disinfectant of the present invention further comprises a zinc-containing compound which releases zinc ion in solution. Such a zinc-containing compound in the disinfectant contributes to enhancing a virucidal activity, especially against adenoviruses. Examples of the zinc-containing compound which releases zinc ion in solution include zinc sulfate, zinc chloride, zinc lactate, zinc acetate, zinc gluconate, zinc stearate and zinc undecylenate. Inter alia, zinc sulfate is preferred.

The content ratio of the zinc-containing compound is usually 0.001 to 0.10 (w/w) relative to the whole disinfectant. Considering poor solubility of the zinc-containing compound in alcohol, it is preferably less than 0.10 (w/w) relative to the whole disinfectant, for easy handling in the pharmaceutical preparation process and the stability of the disinfectant. The content ratio of the zinc-containing compound is preferably about 0.001 to 0.09% (w/w), and more preferably about 0.001 to 0.05% (w/w) relative to the whole disinfectant. When the content ratio is within the above range, the disinfectant has a sufficient antiseptic effect as well as can be used safely for hands and skin.

PH Adjuster

The disinfectant of the present invention may comprise a pH adjuster if needed. The pH adjuster may be any kind as long as it is suitably used in products for skin external use, such as drugs and cosmetics, and is not particularly limited. Examples of such a pH adjuster include alkali metal hydroxides such as sodium hydroxide and potassium hydroxide; salts of an organic acid such as sodium citrate, sodium lactate and sodium succinate; hydroxides of ammonium such as ammonium hydroxide; alkanolamines such as monoethanolamine, diethanolamine, triethanolamine, monoisopropanolamine, diisopropanolamine and triisopropanolamine; alkylamines such as 2-amino-2-methyl-1-propanol and 2-amino-2-methyl-1,3-propanediol; basic amino acids such as lysine and arginine; and POE alkylamines. From a safety viewpoint, salts of an organic acid or salts of an alkali metal are preferred, and salts of an organic acid are more preferred.

As the pH adjuster, organic acids such as tartaric acid, glycolic acid, malic acid, salicylic acid, fumaric acid, methanesulfonic acid, maleic acid, acetic acid and disodium EDTA; or inorganic acids such as hydrochloric acid, phosphoric acid, sulfuric acid, nitric acid and hydrobromic acid, etc. can also be used to the extent that they do not impair the effect of the present invention.

These pH adjusters may be used alone or in combination of two or more kinds. The pH of the disinfectant of the present invention is preferably about 2 to 8, more preferably about 3 to 7, and particularly preferably about 3.5 to 6. When the pH is within the above range, the disinfectant has a sufficient antiseptic effect as well as can be used safely for hands and skin.

Thickener

The disinfectant of the present invention may comprise a thickener to the extent that the thickener does not impair the effect of the present invention. Examples of the thickener include cellulose; cellulose derivatives such as hydroxyethyl cellulose, hydroxypropyl cellulose, hydroxypropylmethyl cellulose, hydrophobized hydroxypropylmethyl cellulose, methyl cellulose and carboxymethyl cellulose sodium; copolymers having acrylic acid or a salt thereof as a constituent, such as cross-linked acrylic acid-starch graft copolymer and N-vinylacetamide/sodium acrylate copolymer; polyvinyl alcohol; polyvinyl pyrrolidone; polyethylene oxide; methyl vinyl ether/maleic anhydride copolymer; polyacrylamide; alginic acid; sodium alginate; propylene glycol alginate; gelatin; gum arabic; gum tragacanth; locust bean gum; guar gum; tamarind gum; xanthan gum; gellan gum; carrageenan; and agar. These thickeners may be used alone or in combination of two or more kinds. Inter alia, hydroxypropylmethyl cellulose or xanthan gum is preferred in respect of the safety and the feeling in use.

Fragrance

The disinfectant of the present invention may comprise a fragrance if needed. The fragrance may be any kind as long as it is suitably used in products for skin external use, such as drugs and cosmetics, and is not particularly limited. Examples of such a fragrance include isopropyl alcohol, eucalyptus oil, geraniol, phenyl ethyl alcohol, linalol and linalyl acetate.

Other Ingredients

The disinfectant of the present invention does not comprise any other microbicidal disinfecting agent intended for microbicidal disinfection than the above ingredients (a) to (d). Examples of such a microbicidal disinfecting agent include acrinol, benzethonium chloride, benzalkonium chloride, benzalkonium cetyl phosphate, cetylpyridinium chloride, methylrosanilinium chloride, iodine, potassium iodide, iodophors such as povidone iodine, iodoform, mercurochrome, alkylpolyaminoethylglycine, thimerosal, bronopol, resorcinol, hinokitiol, triclosan, phenol and derivatives thereof, and chlorhexidine salts such as chlorhexidine gluconate, chlorhexidine acetate and chlorhexidine hydrochloride. The disinfectant of the present invention does not comprise any of the above microbicidal disinfecting agents intended for microbicidal disinfection, and therefore is low irritant to skin.

The disinfectant of the present invention may comprise any known moisturizer that is usually added to microbicidal disinfecting agents. Examples of such a known moisturizer include, for example, silicone oil, fatty acid ester, pyrrolidone carboxylic acid, sodium pyrrolidone carboxylate, sodium lactate, hyaluronic acid, sodium hyaluronate, sodium dl-pyrrolidone carboxylate, urea, propylene glycol and glycerol. Examples of the silicone oil include dimethyl silicone oil, methylphenyl silicone oil and methyl hydrogen silicone oil. Silicone oil has, in addition to moisturizing action, a lubricating action that can make it easy to put on or take off surgical gloves. Examples of the fatty acid ester include isopropyl myristate, isopropyl palmitate, isopropyl stearate, isobutyl oleate and isobutyl maleate. These moisturizers may be used alone or in combination of two or more kinds.

The disinfectant of the present invention may comprise, if needed, one or more kinds selected from the followings: drugs such as glycyrrhizic acid or derivatives thereof, vitamin E, vitamin-E acetate and vitamin $B_6$; nonionic surfactants; amino acids or derivatives thereof; diisobutyl adipate; allantoin; vitamin A derivatives; glycerin fatty acid esters; and fatty acids such as capric acid. These compounds have a protective effect on hands. Addition of a glycerin fatty acid ester and/or a fatty acid such as capric acid provides a spore killing activity and a widened microbicidal spectrum to the disinfectant of the present invention.

Preparation Method

The disinfectant of the present invention can be obtained by mixing all the ingredients, if needed heat-dissolving an ingredient that is in a solid state at ordinary temperature, and usually adjusting the pH of the mixture.

Method for Use

The disinfectant of the present invention can be used for any of daily, hygienic and surgical hand-washing. The method for disinfection may include any commonly-used method, such as the rubbing method and the swab method.

The disinfectant of the present invention may be in the form of, for example, hand lotion, gel, cream or foam.

The disinfectant of the present invention shows a high virucidal and growth-inhibiting activity against non-enveloped viruses such as noroviruses, polioviruses and adenoviruses, and therefore is suitable as a virucidal disinfectant. The disinfectant is particularly useful due to its high virucidal activity even against adenoviruses. Further, the disinfectant can be suitably used for hand disinfection.

Method for Hand Disinfection and Method for Killing Viruses or Inhibiting the Growth Thereof Hand disinfection can be performed by contacting hands with a composition or applying a composition on hands, the composition which comprises the following (a), (b), (c) and (d), but no other microbicidal disinfecting agents intended for microbicidal disinfection:

(a) 40 to 90% (w/w) of ethanol, isopropyl alcohol or a mixture thereof;
(b) 0.1 to 2% (w/w) of lactic acid;
(c) 0.01 to 2% (w/w) of citric acid; and
(d) 0.001 to 0.1% (w/w) of a zinc-containing compound which releases zinc ion in solution, relative to the whole composition.

In the same manner, viruses on hands can be killed or the growth thereof can be inhibited.

Another aspect of the present invention relates to (1) a method for hand disinfection and (2) a method for killing viruses or inhibiting the growth thereof, both of which comprise contacting hands with the above-mentioned composition or applying the same on hands.

The above-mentioned composition to be used in the method for hand disinfection and in the method for killing viruses or inhibiting the growth thereof, and its preferable embodiment are the same as described regarding the aforementioned disinfectant.

The method for contacting hands with the composition or applying the same on hands is the same as described regarding the method for disinfection by use of the aforementioned disinfectant. The examples include any commonly-used method, such as the rubbing method and the swab method.

Use of Composition

As a disinfectant or a virucidal disinfectant, there can be used a composition which comprises the above (a), (b), (c) and (d), but no other microbicidal disinfecting agents intended for microbicidal disinfection.

Another aspect of the present invention relates to (1) use of the above-mentioned composition as a disinfectant and (2) use thereof as a virucidal disinfectant.

The above-mentioned composition in the uses of the present invention and its preferable embodiment are the same as described regarding the aforementioned disinfectant. The method for use of the composition, etc. is the same as that of the aforementioned disinfectant.

Composition for Disinfection

Another aspect of the present invention relates to a composition for disinfection which comprises the above (a), (b), (c) and (d), but no other microbicidal disinfecting agents intended for microbicidal disinfection. Another aspect of the present invention relates to a composition for killing viruses or inhibiting the growth thereof, the composition comprising the above (a), (b), (c) and (d), but no other microbicidal disinfecting agents intended for microbicidal disinfection.

The compositions of the present invention and their preferable embodiment are the same as described regarding the aforementioned disinfectant. The method for use of the compositions, etc. is the same as that of the aforementioned disinfectant.

EXAMPLES

Hereinafter, the present invention will be illustrated in detail by Examples and Test Examples, but the present invention is not limited thereto.

Examples 1 to 3 and Comparative Examples 1 to 12

(1) Preparation of Disinfectant Compositions

All the ingredients shown in Tables 1 and 2 below were mixed with stirring to make the total weight of each composition equal 100 g.

TABLE 1

|  | Example | | | Comparative Example | | | | |
| --- | --- | --- | --- | --- | --- | --- | --- | --- |
|  | 1 | 2 | 3 | 1 | 2 | 3 | 4 | 5 |
| Ethanol | 75 g | 75 g | 75 g | 75 g | 75 g | — | 75 g | 56 g |
| Iso-propyl alcohol | 3.7 g | 3.7 g | 3.7 g | — | — | — | — | — |
| Lactic acid | 1 g | 1 g | 1 g | 1 g | — | 1 g | 1 g | 1 g |
| Citric acid | 0.1 g | 0.1 g | 0.1 g | — | 1 g | 1 g | 1 g | 1 g |
| Zinc sulfate | 0.1 g | 0.1 g | 0.05 g | — | — | — | — | — |
| Sodium lactate | — | — | — | — | — | — | q.s. | q.s. |
| NaOH | — | — | — | q.s. | q.s. | — | — | — |
| Purified water | q.s. | q.s. | q.s. | q.s. | q.s. | q.s. | q.s. | q.s. |
| Total | 100 g | 100 g | 100 g | 100 g | 100 g | 100 g | 100 g | 100 g |
| pH | 3.43 | 3.75 | 3.32 | 4.9 | 4.9 | 4.7 | 4.7 | 2.8 |

TABLE 2

|  | Comparative Example | | | | | |
| --- | --- | --- | --- | --- | --- | --- |
|  | 6 | 7 | 8 | 9 | 10 | 12 |
| Ethanol | 75 g | 75 g | 75 g | 56 g | 50 g | 75 g |
| Isopropyl alcohol | 3.7 g | 3.7 g | 3.7 g | — | — | — |
| Lactic acid | 1 g | 1 g | 1 g | — | — | — |
| Citric acid | 1 g | 1 g | 1 g | 0.001 g | — | — |
| Zinc sulfate | — | — | — | 0.1 g | — | — |
| Sodium lactate | q.s. | q.s. | q.s. | — | — | — |
| NaOH | — | — | — | — | — | — |
| Purified water | q.s. | q.s. | q.s. | q.s. | q.s. | q.s. |
| Total | 100 g | 100 g | 100 g | 100 g | 100 g | 100 g |
| pH | 3.59 | 3.90 | 4.15 | 4.02 | 7.16 | 7.8 |

As a disinfectant of Comparative Example 11, a commercially available 0.2% benzalkonium chloride/ethanol preparation was used. The disinfection of Comparative Example 11 comprises ethanol and propylene glycol, but no organic acids.

(2) Virucidal Activity Against Non-Enveloped Viruses [1]

Test Method

A feline kidney cell line (CRFK cells), JCRB 9035, was infected with an F-9 strain of feline calicivirus (FCV), ATCC VR-782. A feline calicivirus, which is closely related to noroviruses, is commonly used as a norovirus surrogate because the culture method for noroviruses has not been established yet. After the virus fully propagated, the culture supernatant was separated by centrifugation and was used as a viral solution. 10 μL of the viral solution was mixed with 190 μl, of each disinfectant, and then a part of the mixture was sampled at predetermined times and diluted 100-fold with medium to stop the reaction. Then, CRFK cells on a 96-well microplate were infected with the reaction mixture and further cultured.

The efficacy of each disinfectant was determined based on a cytopathogenic effect on the CRFK cells, and decline in the median tissue culture infective dose (TCID50) was expressed as a log reduction value.

The results are shown in the following Table 3 and FIG. 1. PBS (phosphate-buffered saline solution) was used as Control Example.

TABLE 3

|  | Log reduction in TCID50 | | | |
| --- | --- | --- | --- | --- |
|  | contact time (min) | | | |
|  | 0 | 0.5 | 1 | 5 |
| Example 1 | 0.00 | *>4.50 | *>4.50 | *>4.50 |
| Example 2 | 0.00 | *>4.50 | *>4.50 | *>4.50 |
| Example 3 | 0.00 | *>4.00 | *>4.00 | *>4.00 |
| Comparative Example 1 | 0.00 | 1.34 | 1.84 | *>4.00 |
| Comparative Example 2 | 0.00 | 3.67 | 3.84 | *>4.00 |
| Comparative Example 3 | 0.00 | 0.17 | 0.17 | 0.84 |
| Comparative Example 4 | 0.00 | *>4.00 | *>4.00 | *>4.00 |
| Comparative Example 5 | 0.00 | *>4.00 | *>4.00 | *>4.00 |
| Comparative Example 6 | 0.00 | *>4.67 | *>4.67 | *>4.67 |
| Comparative Example 7 | 0.00 | 4.50 | 4.67 | *>4.67 |
| Comparative Example 8 | 0.00 | 3.67 | 3.50 | 3.67 |
| Comparative Example 9 | 0.00 | 3.33 | *>4.67 | *>4.67 |
| Comparative Example 10 | 0.00 | 0.17 | 1.00 | 2.83 |
| Comparative Example 11 | 0.00 | 0.17 | 0.67 | 1.83 |
| Comparative Example 12 | 0.00 | 0.17 | 0.33 | 1.17 |
| Control Example | 0.00 | 0.00 | 0.17 | 0.33 |

*indicates that the virucidal activity reached such an extent that the TCID50 decreased below the detection limit for the virus.

The criterion for the efficacy of the disinfectant is to achieve a 4 log reduction in TCID50 from before to 0.5 minute after contact of the viral solution with the disinfectant.

As shown in Table 3 and FIG. 1, the TCID50 at 0.5 minute post-contact decreased below the detection limit in the disinfectants of Examples 1 to 3.

(3) Virucidal Activity Against Non-Enveloped Viruses [2]

Test Method

A human lung cancer cell line (A549 cells), RCB 0098, was infected with adenovirus type 5 (Adv), ATCC VR-5. After the virus fully propagated, the culture supernatant was separated by centrifugation and was used as a viral solution. 10 μl, of the viral solution was mixed with 190 μl, of each disinfectant, and then apart of the mixture was sampled at predetermined times and diluted 100-fold with medium to stop the reaction. Then, A549 cells on a 96-well microplate were infected with the reaction mixture and further cultured.

The efficacy of each disinfectant was determined based on a cytopathogenic effect on the A549 cells, and decline in the median tissue culture infective dose (TCID50) was expressed as a log reduction value.

The results are shown in the following Table 4 and FIG. 2. PBS (phosphate-buffered saline solution) was used as Control Example.

TABLE 4

| | Log reduction in TCID50 | | | |
|---|---|---|---|---|
| | 0 | 0.5 | 1 | 5 |
| Example 1 | 0.00 | *>5.00 | *>5.00 | *>5.00 |
| Example 2 | 0.00 | *>5.00 | *>5.00 | *>5.00 |
| Example 3 | 0.00 | 5.00 | *>5.33 | *>5.33 |
| Comparative Example 4 | 0.00 | 1.66 | 1.66 | 2.16 |
| Comparative Example 5 | 0.00 | 1.67 | 1.67 | 3.00 |
| Comparative Example 6 | 0.00 | 1.00 | 2.83 | *>5.33 |
| Comparative Example 7 | 0.00 | 0.66 | 1.33 | *>5.33 |
| Comparative Example 8 | 0.00 | 0.66 | 1.00 | 5.00 |
| Comparative Example 9 | 0.00 | 1.17 | 1.33 | 1.67 |
| Comparative Example 10 | 0.00 | 0.17 | 1.33 | 4.17 |
| Comparative Example 11 | 0.00 | 2.33 | 3.17 | *>5.00 |
| Comparative Example 12 | 0.00 | 0.17 | 3.17 | *>5.00 |
| Control Example | 0.00 | 0.00 | -0.17 | -0.33 |

*indicates that the virucidal activity reached such an extent that the TCID50 decreased below the detection limit for the virus.

The criterion for the efficacy of the disinfectant is to achieve a 4 log reduction in TCID50 from before to 0.5 minute after contact of the viral solution with the disinfectant.

As shown in Table 4 and FIG. 2, the TCID50 at 0.5 minute post-contact decreased below the detection limit in the disinfectants of Examples 1 and 2. The TCID50 at 1 minute post-contact decreased below the detection limit in the disinfectant of Example 3.

These results demonstrated that incorporation of a zinc-containing compound in disinfectants enhanced an inactivating effect (virucidal effect) on adenoviruses.

On the other hand, the disinfectants of Comparative Examples 4 to 12 showed some reduction in TCID50 at 0.5 or 1 minute post-contact, but failed to achieve the practical efficacy criterion of a 4 log reduction.

INDUSTRIAL APPLICABILITY

The disinfectant of the present invention is highly effective against non-enveloped viruses such as noroviruses, polioviruses and adenoviruses, against which disinfectant ethanol is ineffective.

The disinfectant of the present invention also has an extremely excellent fast-acting and persistent effect, and thereby can provide sufficient disinfection on hands without frequent use. Therefore, the disinfectant can prevent hands from skin roughness caused by frequent use of alcoholic disinfectants, and can be used suitably for hand disinfection.

The invention claimed is:

1. A method for hand disinfection, which comprises contacting hands with a composition or applying a composition on hands, the composition comprising the following (a), (b), (c) and (d), but no other microbicidal disinfecting agents intended for microbicidal disinfection:
   (a) 50 to 90% (w/w) of ethanol, isopropyl alcohol or a mixture thereof;
   (b) 0.1 to 2% (w/w) of lactic acid;
   (c) 0.01 to 2% (w/w) of citric acid; and
   (d) about 0.001 (w/w) to 0.1% (w/w) of a zinc-containing compound which releases zinc ion in solution, relative to the whole disinfectant.

2. A method for killing a virus or inhibiting the growth thereof, which comprises contacting hands with a composition or applying a composition on hands, the composition comprising the following (a), (b), (c) and (d), but no other microbicidal disinfecting agents intended for microbicidal disinfection:
   (a) 50 to 90% (w/w) of ethanol, isopropyl alcohol or a mixture thereof;
   (b) 0.1 to 2% (w/w) of lactic acid;
   (c) 0.01 to 2% (w/w) of citric acid; and
   (d) about 0.001 (w/w) to 0.1 (w/w) of a zinc-containing compound which releases zinc ion in solution, relative to the whole disinfectant.

3. The method according to claim 2, wherein the concentration of the zinc-containing compound which releases zinc ion in solution is about 0.001 to 0.05% (w/w) relative to the whole disinfectant.

4. A method for enhancing a fast-acting and persistent effect against adenovirus and norovirus to a disinfectant comprising (a) 50 to 90% (w/w) of ethanol, isopropyl alcohol or a mixture thereof, (b) 0.1 to 2% (w/w) of lactic acid and (c) 0.01 to 2% (w/w) of citric acid, relative to the whole disinfectant, but no other microbicidal disinfecting agents intended for microbicidal disinfection, the method comprising adding to the disinfectant (d) about 0.001 (w/w) to 0.1% (w/w) of a zinc-containing compound which releases zinc ion in solution, relative to the whole disinfectant.

5. The method according to claim 1, wherein hands are rubbed with the composition as defined in claim 1.

6. The method according to claim 2, wherein hands are rubbed with the composition as defined in claim 2.

7. The method according to claim 2, wherein the virus is adenovirus or norovirus.

8. The method according to claim 2, wherein the virus is adenovirus.

* * * * *